United States Patent [19]

Tuba et al.

[11] 4,171,306

[45] Oct. 16, 1979

[54] DIEPOXY-ANDROSTANES AND A PROCESS FOR THE PREPARATION THEREOF

[75] Inventors: Zoltan Tuba; Maria Marsai, both of Budapest, Hungary

[73] Assignee: Richter Gedeon Vegyeszeti Gyar Rt., Budapest, Hungary

[21] Appl. No.: 762,234

[22] Filed: Jan. 25, 1977

Related U.S. Application Data

[63] Continuation-in-part of Ser. No. 702,051, Jul. 2, 1976, abandoned, Ser. No. 702,050, Jul. 2, 1976, abandoned, Ser. No. 709,323, Jul. 28, 1976, Pat. No. 4,071,515, Ser. No. 709,325, Jul. 28, 1976, Pat. No. 4,101,545, and Ser. No. 762,233, Jan. 25, 1977, Pat. No. 4,110,326.

[30] Foreign Application Priority Data

Jul. 15, 1975 [HU] Hungary .............................. RI 571

[51] Int. Cl.$^2$ ............................................. C07J 21/00
[52] U.S. Cl. ......................... 260/239.55 R; 260/397.4; 260/397.5
[58] Field of Search .................... 260/239.55 R, 397.4, 260/397.5

[56] References Cited

U.S. PATENT DOCUMENTS 4,071,515  1/1978  Tuba et al. .................. 260/239.55 R

FOREIGN PATENT DOCUMENTS 1398050  6/1975  United Kingdom ................ 260/239.55

*Primary Examiner*—Elbert L. Roberts
*Attorney, Agent, or Firm*—Karl F. Ross

[57] ABSTRACT

5α, 17B-Diacetoxy-6 -chloro-2α, 3α; 16α, 17α-diepoxy-androstane; 5α, 17B-Dicetoxy-6 -chloro-androsta-2,16-diene; 5α-Hydroxy-6 -chloro-17-oxo-androst-2-ene or a like intermediate in the production of curare-like compounds is produced by reacting 5α, 6B-dihydroxy-17-oxo-androst-2-ene with an organic sulfonic acid chloride. The obtained 5α- hydroxy-6B-chloro-17-oxo-androst-2-ene can then be reacted with the enol acetate of a ketone having 3 to 5 carbon atoms to yield 5α, 17B-diacetoxy-6B-chloro-androsta-2,16-diene. The latter is treated to yield the corresponding diepoxide.

9 Claims, No Drawings

DIEPOXY-ANDROSTANES AND A PROCESS FOR THE PREPARATION THEREOF

CROSS REFERENCE TO RELATED APPLICATIONS

This application is a continuation in part of Ser. No. 702,051 filed 2 July 1976 and a continuation-in-part of Ser. No. 702,050 filed 2 July 1976 both now abandoned and a continuation-in-part of commonly owned copending applications Ser. Nos. 709,323 now Pat. No. 4,071,515 and 709,325 now Pat. No. 4,101,545 both filed 28 July 1976. The application is also a continuation-in-part of pending application Ser. No. 762,233 filed Jan. 25, 1977, now Pat. No. 4,110,326.

The invention relates to a new compound 5α,17B-diacetoxy-6B-chloro-2α, 3α; 16α, 17α-diepoxy-androstance and to a process for the preparation thereof.

The new compound of the invention is a valuable intermediate product in the synthesis of new steroid compounds having curare-like activity.

The new compound 5α,17B-diacetoxy-6B-chloro-2α,3α; 16α,17α-diapoxy-androstane is prepared according to the invention by reacting 5α,17B-dihydroxy-17-oxoandrost-2-ene with an organic sulfonic acid chloride, preferably with methanesulfonic acid chloride and then reacting the obtained 5α-hydroxy-6B-chloro-17-oxo-androst-2-ene, optionally in the presence of an acid catalyst, with an enol acetate of an aliphatic ketone having 3 to 5 carbon atoms, converting the obtained 5α,17B-diacetoxy-6B-chloro-androsta-2,16-diene into the corresponding diepoxide by treating it with an organic peracid and finally isolating the desired product from the reaction mixture.

The 5α,6B-dihydroxy-17-oxo-androst-2-ene used as the starting material is a known compound (of J. Org. Chem., 4, 506 (1939); Tetrahedron Letters 27, 1517-1526 (1971)).

The intermediate compounds of the present synthesis described below are new compounds not described hitherto in the literature.

More particularly, the new compound of the invention is prepared in the following way:

The 5α, 6B-dihydroxy-17-oxo-androst-2-ene is reacted in the presence of an organic tertiary base, preferably pyridine, an organic sulfonic acid chloride, preferably with methane sulfonic acid chloride.

This reaction is carried out at a temperature between 10° C. and 50° C., preferably at 20° C. to 30° C. The obtained 5α-hydroxy-6B-chloro-derivative is recovered from the reaction mixture e.g. by precipitation with water.

This compound is then reacted, in the presence of sulfuric acid or an organic sulfonic acid, preferably p-toluene sulfonic acid with the enol acetate of an aliphatic ketone having 3 to 5 carbon atoms, preferably isopropenyl acetate. This reaction is performed at elevated temperature, preferably at the boiling temperature of the reaction mixture, and the aliphatic ketone having 3 to 5 carbon atoms, which is liberated in this reaction, is continuously distilled off.

The 5α, 17B-diacetoxy-6B-chloro-androsta-2,6-diene obtained as reaction product is then extracted from the distillation residue with an aliphatic ether or chlorinated hydrocarbon, and can be purified, if desired, by an adsorption method, preferably by column chromatography and/or by recrystallization from an aliphatic alcohol having 1 to 3 carbon atoms.

The epoxidation of the thus obtained 5α, 17B-diacetoxy-derivative is then performed with an organic peracid, preferably with perbenzoic acid or m-chloroperbenzoic acid in the presence of an inert organic solvent, e.g. benzene or ether.

The reaction is carried out at a temperature between −5° C. and 30° C., preferably at 10°-20° C. The excess of the acid is removed from the reaction mixture by heating it with a base, preferably an alkali hydroxide solution and then with water. The organic phase is then separated from the aqueous phase and the former is then evaporated. The evaporation residue can be purified, if desired, by crystallisation.

The process of the invention is illustrated in more detail by the following non-limiting examples.

EXAMPLE 1

5α-Hydroxy-6B-chloro-17-oxo-androst-2-ene 50 g. (0.16 mol.) of 5α,6B-dihydroxy-17-oxo-androst-2-ene are dissolved in 500 ml. of anhydrous pyridine, and 30 g. (0.26 mol.) of methanesulfonic acid are added to the solution. The mixture is allowed to stand at room temperature for 16 hours and then poured into 5 liters of ice water. The precipitated crude product is separated by filtration, washed with aqueous 10 percent hydrochloric acid until free of pyridine, then with water until neutral and then dried in vacuo over phosphorous pentoxide. The so-obtained product is dissolved in twenty fold quantity of acetone and clarified by stirring with 100 g. of silica gel. The mixture is filtered; the filtrate is concentrated to a syrup. The precipitated product is separated by filtration and dried to yield 47 g. 5α-hydroxy-6B-chloro-17-oxo-androst-2-ene (88% of theory). M.P. 178°-180° C.; $(\alpha)_D^{25} = +59°$ C. (c=1, in chloroform).

Analysis for $C_{19}H_{27}ClO_2$: calculated: C 70.6%, H 8.60%, Cl 11.0%; found: C 70.4%, H 8.63%, Cl 10.8%.

The 5α,6B-dihydroxy-17-oxo-androst-2-ene used as starting material is prepared in the following way:

250 g. (0.87 mol.) of 3B-hydroxy-17-oxo-androst 5-ene are dissolved in 2500 ml. of chloroform, and 198 g. (1.01 mol.) 88% m-chloro-perbenzoic acid are added to the solution. The reaction mixture is stirred for 1 hour at a temperature below 33° C., and the solution of 75 g. sodium hydroxide in 5 liters of water is added thereto. After stirring the phases are separated. The chloroform phase is shaken out with a further portion of sodium hydroxide solution to reach pH=7, and then with water. After separating the phases again, the chloroform phase is dried over sodium sulfate and then the chloroform is distilled off. The obtained residue is a mixture of 3B-hydroxy-5α, 6α-epoxy-17-oxo-androstane and 3B-hydroxy-5B, 6B-epoxy-17-oxo-androstane. This mixture of the isomeric products is then mixed with a tenfold quantity of ether and filtered. 234 g. of the mixture of isomers (90% of theory) is obtained; m.p. 197°-200° C.

Analysis for $C_{19}H_{28}O_3$: calculated: C 75.00%, H 9.22%; found: c 74.70%, H 8.98%.

275 g. (0.905 mol.) of the above-obtained mixture of isomers are dissolved in 2150 ml. of dioxane. 725 ml. of 10% perchloric acid solution are added in small portions within 20 minutes. The reaction mixture is stirred at room temperature for 1.5 hours, then it is poured to 7 liters of icy 20% sodium chloride solution. The precipitated product is separated by filtration and washed with 500 ml. of water. The mother liquor is saturated with sodium chloride, and the saturated solution is allowed to stand over night at 0° C. to 5° C. The precipitated second crop of the product is separated by filtration, combined with the above-obtained first crop; the product is dried and purified by suspension in a tenfold quantity of ether. 263 g. of 3B, 5α6B-tryhydroxy-17-oxo-androstane (95% of theory) are obtained; m.p. 304°–306° C.

Analysis for $C_{19}H_{30}O_4$: calculated: C 70.80%, H 9.33%; found: C 70.71%, H 9.08%.

100 g (0.31 mol.) of the above-obtained trihydroxy derivative are dissolved in 1000 ml. of anhydrous pyridine, and 89 g. (0.466 mol.) of p-toluene-sulfonic acid chloride are added to the solution. The reaction mixture is allowed to stand for 48 hours at 0° C. to 5° C., and then poured into 10 liters of ice water. The precipitated product is filtered off, washed with an aqueous 3–4% hydrochloric acid solution, and with water to remove residual traces of pyridine, and then dried in vacuo over phosphorus pentoxide, at max. 40° C. The product can be purified, if desired, by suspension in a tenfold quantity of ether. 138 g. of 3B-tosylocy-5 6B-dihydroxy-17-oxo-androstance (93% of theory) are obtained; m.p. 154°–156° C.; $(\alpha)_D^{25}=0°$ C. (c=1, in chloroform).

Analysis for $C_{26}H_{36}O_6S$: calculated: C 65.40%, H 7.55%, S 6.70%; found: C 65.41%, H 7.29%, S 6.50%.

70 g. (0.147 mol.) of the above-obtained 3B-tosyloxy-5α, 6B-dihydroxy-17-oxo-androstane are dissolved in 350 ml. of collidine, and the mixture is stirred in a nitrogen atmosphere for 1.5 hours at 160° C. The collidine is then distilled off at reduced pressure; the residue is triturated with 400 ml. of water, filtered and washed first with aqueous 10% hydrochloric acid solution and then with water to remove any residual traces of collidine. The obtained product is dried in vacuo over phosphorus pentoxide at 40° C., and, if desired, by suspension in a fivefold quantity of diethyl ether.

45 g. of 5α, 6B-dihydroxy-17-oxo-androst-2-ene (90% of theory); m.p. 183°–186° C.; $(\alpha)_D^{25}=+81°$ C. (c=1, in chloroform).

Analysis for $C_{19}H_{28}O_3$: calculated: C 75.00%, H 9.22%; found: C 75.10%, H 9.07%.

EXAMPLE 2

5α, 17B-Diacetoxy-6B-chloro-androsta-2, 16 diene 30 g. (0.09 mol.) 5α-hydroxy-6B-chloro-17-oxo-androst-2-ene are dissolved in 60 ml freshly distilled isopropenyl acetate, and 1.5 g. p-toluenesulfonic acid are added to the solution. Under a 80 cm. long mirror-column filled with Rasching-rings, the reaction mixture is heated uniformly to reach the boiling temperature of the mixture in 1.5 hours, and then the acetone formed in the reaction is distilled off continuously. After 8 hours of distillation the reaction mixture is cooled to room temperature and then poured into 3500 ml. of ice water. The separated oily product is extracted with 2×300 ml of ether, the combined ether extracts are cooled to a temperature between 0° C. and 5° C., and the ether solution is washed under ice-cooling with aqueous 5% sodium-hydroxide solution to reach the pH-value of 7. The ether phase is then separated, dried with sodium sulfate, filtered, and then the ether and the unreacted excess of isopropenyl acetate are distilled off. The oily residue is chromatographed on a column filled with 180 g. silica gel having a particle size of 0.003 to 0.200 mm. The column is eluted with hexane containing 5% ether. The eluate fractions are analysed by thin layer chromatography (on silica gel plates, with a 8:2 mixture of benzene and acetone); the fractions containing the desired product are combined and evaporated. The evaporation residue is crystallized from methanol. 25 g. 5α, 17B-diacetoxy-6B-chloro-androsta-2, 16-diene (74% of theory) are obtained; m.p. 127°–129° C.; $(\alpha)_D^{25}=-14,8°$ C. (c=1, in chloroform).

Analysis for $C_{23}H_{31}ClO_4$: Calculated: C 67.8%, H 7.6%, Cl 8.7%; found: C 67.7%, H 7.3%, Cl 8.5%.

EXAMPLE 3

20.5 g (0.054 mol.) of 5α, 17B-diacetoxy-6B-chloro-androsta-2, 16-dien are dissolved in 100 ml. of benzene, and 400 ml. of a 7% solution of perbenzoic acid in ether (0.20 mol. (are added thereto. The reaction mixture is allowed to stand at room temperature for 24 hours and then cooled to 0° C. to 5° C. an washed with an aqueous 7% sodium hydroxide solution an then with water to reach the pH-value of 7. The phases are separated; the organic phase is dried over sodium sulfate and the solvent is distilled off. The distillation residue is triturated with ether, filtered and dried. 16.8 g. of 2α, 3α; 16α, 17α-diepoxy-5α, 17B-diacetoxy-6B-chloro-androsane (76% of theory) are obtained; m.p. 164°–168° C. $(\alpha)_D^{25}=-1.1°$ C. (c=1, in chloroform).

Analysis for $C_{23}H_{31}ClO_6$: Calculated: C 62.9%, H 7.0%, Cl 8.0%; found: C 62.68%, H 7.11%, Cl 7.9%.

What we claim is:

1. A compound selected from the group which consists of 5α, 17B-Diacetoxy-6B-chloro-2α, 3α; 16α, 17α-diepoxy-androstane; 5α, 17B-Diacetoxy-6B-chloro-androsta-2, 16-diene; and 5α-Hydroxy-6-B-chloro-17-oxo-androst-2-ene.

2. A process for the preparation of 5α, 17B-diacetoxy-6B-chloro-2α, 3α, 17α-diepoxy-androstane, which comprises reacting 5α, 6B-dihydroxy-17-oxo-androst-2-ene with an organic sulfonic acid chloride, reacting the obtained 5α-hydroxy-6B-chloro-17-oxo-androst-2-ene with isopropenyl acetate and treating the obtained 5α, 17B-diacetoxy-6B-chloro-androsta-2, 16-diene with an organic peracid to yield the corresponding diepoxide.

3. A process as claimed in claim 2, wherein methanesulfonic acid chloride is used as organic sulfonic acid chloride.

4. A process as claimed in claim 2, wherein the reaction of 5α, 6B-dihydroxy-17-oxo-androst-2-ene with the organic sulfonic acid chloride is performed at a temperature between −10° C. and 50° C.

5. A process as claimed in claim 2, wherein the 5α-hydroxy-6B-chloro-17-oxo-androst-2-ene is reacted with isopropenyl the in the presence of an acid catalyst.

6. A process as claimed in claim 5, wherein an organic sulfonic acid, preferably an aromatic sulfonic acid is used as 7. A process as claimed in claim 2, wherein the reaction of 5α-hydroxy-6B-chloro-17-oxo-androst-2-ene with isopropenyl is carried out at the boiling point of the reaction mixture.

8. A process for producing a 5α-hydroxy-6B-chloro-17-oxo-androst-2-ene which comprises reacting 5α, 6B-dihydroxy-17-oxo-androst-2-ene with an organic sulfonic acid chloride.

9. A process for the preparation of 5α, 17β-diacetoxy-6β-chloro-2α,3α; 16α, 17α-diepoxy-androstane, which comprises reacting 5α, 6β-dihydroxy-17-oxo-androst-2-ene with an organic sulfonic acid chloride, reacting the obtained 5α-hydroxy-6β-chloro-17-oxo-androst-2-ene with a $C_3$ to $C_5$ isoalkenyl acetate and treating the obtained 5α, 17β-diacetoxy-6β-chloro-androsta-2,16-diene with an organic peracid to yield the corresponding diepoxide.

* * * * *